(12) United States Patent
Hong et al.

(10) Patent No.: US 8,734,890 B2
(45) Date of Patent: May 27, 2014

(54) METHOD FOR FORMING A MOLECULARLY IMPRINTED POLYMER BIOSENSOR

(75) Inventors: Chien-Chong Hong, Hsinchu County (TW); Po-Hsiang Chang, Kaohsiung (TW); Chih-Chung Lin, Taoyuan County (TW)

(73) Assignee: National Tsing Hua University, Hsinchu (TW)

( * ) Notice: Subject to any disclaimer, the term of this patent is extended or adjusted under 35 U.S.C. 154(b) by 858 days.

(21) Appl. No.: 12/889,494

(22) Filed: Sep. 24, 2010

(65) Prior Publication Data

US 2011/0241260 A1 Oct. 6, 2011

Related U.S. Application Data

(63) Continuation-in-part of application No. 12/560,836, filed on Sep. 16, 2009.

(30) Foreign Application Priority Data

May 19, 2010 (TW) ................................ 99115949 A

(51) Int. Cl.
*A61L 33/00* (2006.01)

(52) U.S. Cl.
USPC .......... 427/2.11; 522/152; 427/510; 427/2.13; 427/2.1; 436/94; 604/890.1; 382/284; 210/500.34; 210/500.27; 210/502.1; 210/638; 430/269

(58) Field of Classification Search
USPC ......................... 351/163; 430/269, 296, 942; 210/500.34, 500.35, 500.42; 382/284; 604/890.1; 436/94; 522/152; 427/510, 427/508

See application file for complete search history.

(56) References Cited

U.S. PATENT DOCUMENTS

| | | | | |
|---|---|---|---|---|
| 5,587,273 | A * | 12/1996 | Yan et al. | 430/269 |
| 7,184,610 | B2 * | 2/2007 | Weinstein et al. | 382/284 |
| 7,279,096 | B2 * | 10/2007 | Murray | 210/500.34 |
| 2002/0035167 | A1 * | 3/2002 | Beuhler et al. | 522/152 |
| 2003/0153900 | A1 * | 8/2003 | Aceti et al. | 604/890.1 |
| 2006/0102556 | A1 * | 5/2006 | Piletsky et al. | 210/500.34 |

OTHER PUBLICATIONS

Ghatak et al., Adhesion Induced Instability Patterns in Thin Confined Elastic Films, 2003, Langmuir, vol. 19, pp. 2621-2631.*
Petcu et al., Propofol Imprinted Membranes with Potenetial Applications in Biosensors, 2004, Analytica Chimica Acta, vol. 504, pp. 73-79.*

* cited by examiner

*Primary Examiner* — Dah-Wei D Yuan
*Assistant Examiner* — Andrew Bowman
(74) *Attorney, Agent, or Firm* — Birch, Stewart, Kolasch & Birch, LLP

(57) ABSTRACT

A method for forming a molecularly imprinted polymer biosensor includes: (a) preparing a reaction solution including an imprinting molecule, a functional monomer, an initiator, and a crosslinking agent; (b) disposing the reaction solution in a space between upper and lower substrates each of which is made of a light-transmissible material; (c) disposing on the upper substrate a photomask having a patterned hole; (d) irradiating the reaction solution through the patterned hole of the photomask and the upper substrate so that the reaction solution undergoes polymerization to form a polymer between the upper and lower substrates; (e) removing the upper substrate after the polymer is formed on the lower substrate; and (f) extracting the imprinting molecule from the polymer so that a patterned molecularly imprinted polymer film is formed on the lower substrate.

13 Claims, 5 Drawing Sheets

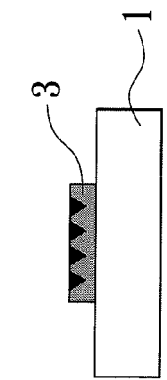
FIG. 1(a)
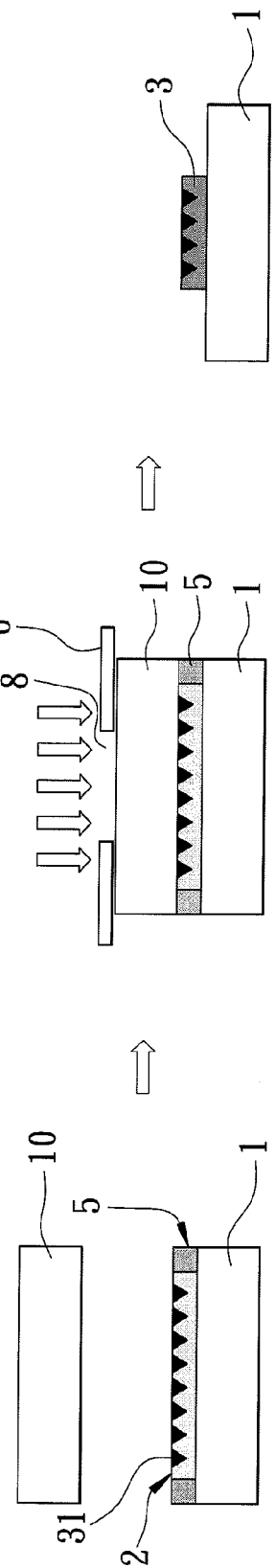
FIG. 1(b)
FIG. 1(c)
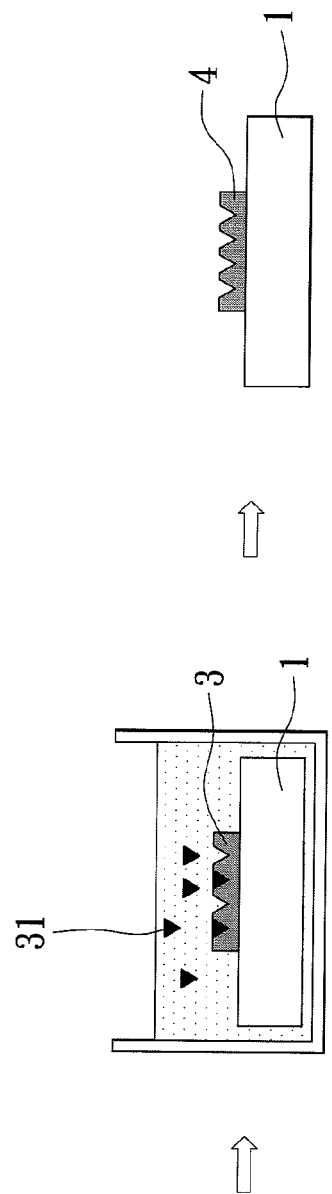
FIG. 1(d)
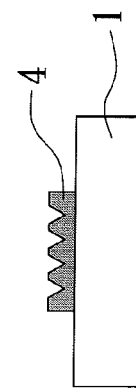
FIG. 1(e)

METHOD FOR FORMING A MOLECULARLY IMPRINTED POLYMER BIOSENSOR

CROSS-REFERENCE TO RELATED APPLICATION

This application is a continuation-in-part (CIP) of U.S. patent application Ser. No. 12/560,836, filed on Sep. 16, 2009.

This application claims priority of Taiwanese application no. 099115949, filed on May 19, 2010.

BACKGROUND OF THE INVENTION

1. Field of the Invention

This invention relates to a method for forming a molecularly imprinted polymer biosensor, more particularly to a method for forming a molecularly imprinted polymer film biosensor that is used for detecting an anesthetic.

2. Description of the Related Art

Molecularly imprinted polymer (MIP) biosensors are widely used in many applications, such as separations or extractions, artificial antibodies, catalysts, biosensors, and so on. Currently, a MIP film of the MIP biosensor is primarily made by preparing a reaction solution including an imprinting molecule (which has functional groups and a size similar to or the same as those of a target molecule), a functional monomer, a crosslinking agent, and an initiator; coating the reaction solution onto a substrate; curing and polymerizing the reaction solution to form a polymer film on the substrate; and extracting the imprinting molecule from the polymer film to form the MIP film having a plurality of recognition sites for binding to the target molecules.

A method for molecularly imprinting a material is disclosed in U.S. Pat. No. 5,587,273 and comprises: (1) coating a solution on a silicon wafer, the solution including a solvent, a polymeric material capable of undergoing an addition reaction with a nitrene, a crosslinking agent, a functional monomer, and an imprinting molecule; (2) evaporating the solvent to leave a residue; (3) exposing the residue to an energy source, thereby forming a crosslinked polymeric substrate; and (4) extracting the imprinting molecule from the crosslinked polymeric substrate. However, there is no discussion concerning how to improve the performance (e.g., adsorption specificity, sensitivity, and linearity between sensing voltages and concentrations of the target polymers, etc.) of the MIP film.

In the past, in order to improve the adsorption specificity of the conventional MIP film, the MIP film is preferably formed with a plurality of pores for increasing a surface area adapted to be placed in contact with the target molecules. Besides, the pores have a pore size that only permits passing of the target molecules. The pores of the MIP film can be increased by grinding or by adding a porogen in the solution. However, both of the methods for forming pores in the NIP film are likely to unfavorably destroy the recognition sites in the MIP film.

SUMMARY OF THE INVENTION

Therefore, an object of the present invention is to provide a method for forming a molecularly imprinted polymer biosensor, in which a molecularly imprinted polymer film has a plurality of pores with appropriate sizes, can exhibit an adsorption specificity corresponding to anesthetics in different concentrations, and can exhibit relatively good sensitivity when used in the molecularly imprinted polymer biosensor for detecting the target molecules.

Accordingly, a method for forming a molecularly imprinted polymer biosensor of the present invention comprises:

(a) preparing a reaction solution including an imprinting molecule, a functional monomer, an initiator, and a crosslinking agent;

(b) disposing the reaction solution in a space between upper and lower substrates each of which is made of a light-transmissible material;

(c) disposing on the upper substrate a photomask having a patterned hole;

(d) irradiating the reaction solution through the patterned hole of the photomask and the upper substrate so that the reaction solution undergoes polymerization to form a polymer between the upper and lower substrates;

(e) removing the upper substrate after the polymer is formed on the lower substrate; and (f) extracting the imprinting molecule from the polymer so that a patterned molecularly imprinted polymer film is formed on the lower substrate.

BRIEF DESCRIPTION OF THE DRAWINGS

Other features and advantages of the present invention will become apparent in the following detailed description of the preferred embodiment of the invention, with reference to the accompanying drawings, in which:

FIGS. 1(a) to 1(e) show consecutive steps of the preferred embodiment of a method for forming a molecularly imprinted polymer biosensor according to the present invention;

DETAILED DESCRIPTION OF THE PREFERRED EMBODIMENT

Figure 2:
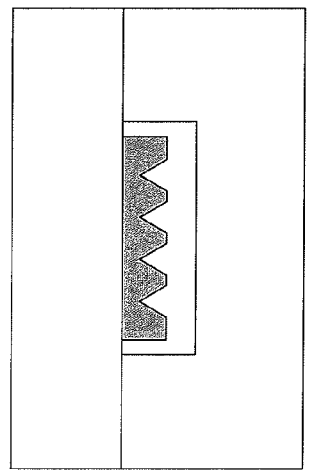
FIG. 2 shows a step of bonding a microchannel substrate to a lower substrate of the molecularly imprinted polymer biosensor formed by the preferred embodiment of FIG. 1.
Figure 2:
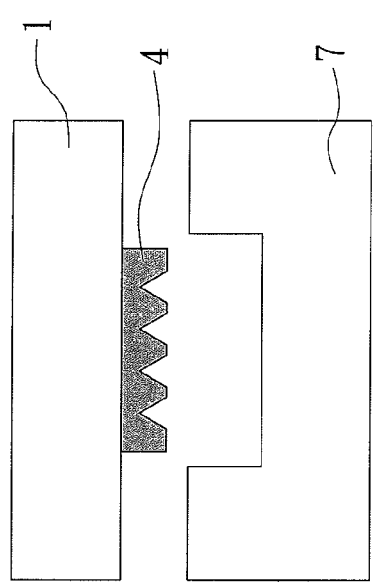

Referring to FIGS. 1 (a) to 1(e), the preferred embodiment of a method for forming a molecularly imprinted polymer (MIP) biosensor of the present invention includes: (a) preparing a reaction solution 2 including an anesthetic 31 serving as an imprinting molecule, a functional monomer, an initiator, and a crosslinking agent; (b) disposing the reaction solution 2 in a space between lower and upper substrates 1, 10 by adding the reaction solution 2 dropwise on a top face of the lower substrate 1 confined by a spacer 5, followed by disposing the upper substrate 10 onto the lower substrate 1 with the spacer 5 therebetween (see FIG. 1(a)); (c) disposing on the upper substrate 10 a photomask 6 having a patterned hole 8 and irradiating the reaction solution 2 through the patterned hole 8 of the photomask 6 and the upper substrate 10 so that the reaction solution 2 undergoes polymerization to form a polymer 3 between the lower and upper substrates 1, 10 (see FIG. 1(b)); (d) removing the photomask 6, the upper substrate 10 and the spacer 5 after the polymer 3 is formed on the lower substrate 1 (see FIG. 1(c)); and (e) extracting the anesthetic 31 from the polymer 3 to form a patterned molecularly imprinted polymer film (MIP film) 4 (see FIGS. 1(d) and 1(f)).

Each of the lower and upper substrates 1, 10 is made of a light-transmissible plastic material. Use of the light-transmissible plastic material may reduce the production cost and may favor subsequent applications in addition to enhancement of the solvent resistance of the lower and upper substrates 1, 10. Preferably, the light-transmissible plastic material is a material having improved chemo-resistance and physical properties and a relatively high transmittance, such as cyclic olefin copolymer (COC).

The anesthetic 31 is preferably selected from liquid anesthetics of small molecules, such as 2,6-diisopropylphenol (propofol).

The functional monomer has at least one functional group capable of interacting, either covalently or non-covalently, with the anesthetic 31. Preferably, the functional monomer is mathacrylic acid.

Examples of the crosslinking agent may include, but are not limited to, ethylene glycol dimethacrylate (EGDMA) and divinylbenzene (DVB).

Examples of the initiator may include, but are not limited to, 2,2-azobisisobutyronitrile (AIBN) and 1,1-azobiscyclohexanecarbonitrile (ABCN). In one embodiment of the present invention, the initiator is ABCN.

Preferably, the molar ratio of the anesthetic 31, the functional monomer, the crosslinking agent and the initiator with respect to each other in the reaction solution ranges from about 1:4:30:0.17 to 1:4:30:0.85, and, more preferably, ranges from about 1:4:30:0.30 to 1:4:30:0.50. In one embodiment of the present invention, the molar ratio is 1:4:30:0.41. When the molar ratio of the initiator with respect to the anesthetic 31, the functional monomer, and the crosslinking agent is lower than 0.17, the polymer 3 cannot satisfactorily polymerized. On the other hand, when the molar ratio of the initiator with respect to the anesthetic 31, the functional monomer, and the crosslinking agent is more than 0.85, a crack or a crystal-like structure is likely to be formed in the polymer 3 and the MIP film 4 subsequently formed such that light-transmittance of the MIP film 4 is adversely affected.

Preferably, in the step (c), the polymerization of the reaction solution 2 is conducted with an irradiation energy ranging from 16 J/cm$^2$ to 72 J/cm$^2$.

Besides, a solvent, such as toluene, and a porogen used in fabrication of the conventional molecularly imprinted polymer (MIP) biosensors can be excluded from the reaction solution.

The pattern of the patterned hole 8 of the photomask 6 may vary based on the practical requirements. Only the reaction solution 2 exposed from the patterned hole 8 of the photomask 6 (see FIG. 1(b)) is polymerized to form the polymer 3 on the lower substrate 1. When the photomask 6 having a plurality of patterned holes 8 is used, a plurality of polymer units, each of which consists of the polymer 3 and has a pattern corresponding to the corresponding one of the patterned holes 8, are formed from the reaction solution 2. Hence, a plurality of MIP films 4 are subsequently formed from the polymer units.

In the step (e), the anesthetic 31 can be extracted by a conventional method. Preferably, the anesthetic 31 is extracted using an extracting reagent. Preferably, the extracting reagent is methanol.

Preferably, the MIP film 4 has a thickness ranging from 25 μm to 75 μm.

Preferably, the MIP film 4 on the lower substrate 1 has a plurality of pores with a pore size ranging from 10 nm to 30 nm.

Additionally, the pores having a proper pore size can be formed by the method for forming a molecularly imprinted polymer (MIP) biosensor according to the present invention without grinding and the use of a solvent or porogen. Consequently, damage to recognition sites of the MIP films 4 caused by grinding, the solvent or porogen may be avoided so as to improve adsorption specificity of the MIP films 4.

Referring to FIG. 2, the method of this invention illustrated in FIG. 1 may further include thermally bonding the lower substrate 1 with the MIP film 4 to a microchannel substrate 7. The microchannel substrate 7 is formed with a micro-fluid channel to receive the MIP film 4 on the lower substrate 1 and is made of a plastic material. In particular, since the lower substrate 1 having the MIP film 4 and the microchannel substrate 7 may be both made of the plastic material, they may be bonded to each other using a thermal pressing process without using an adhesive. Accordingly, compared to the prior art, the bonding of the lower substrate 1 to the microchannel substrate 7 in the process for making the MIP biosensor can be simplified and the MIP biosensor thus made can exhibit relatively good sensitivity.

The present invention is explained in more detail below by way of the following examples. It should be noted that the examples are only for illustration and not for limiting the scope of the present invention.

EXAMPLE 1

Figure 3:
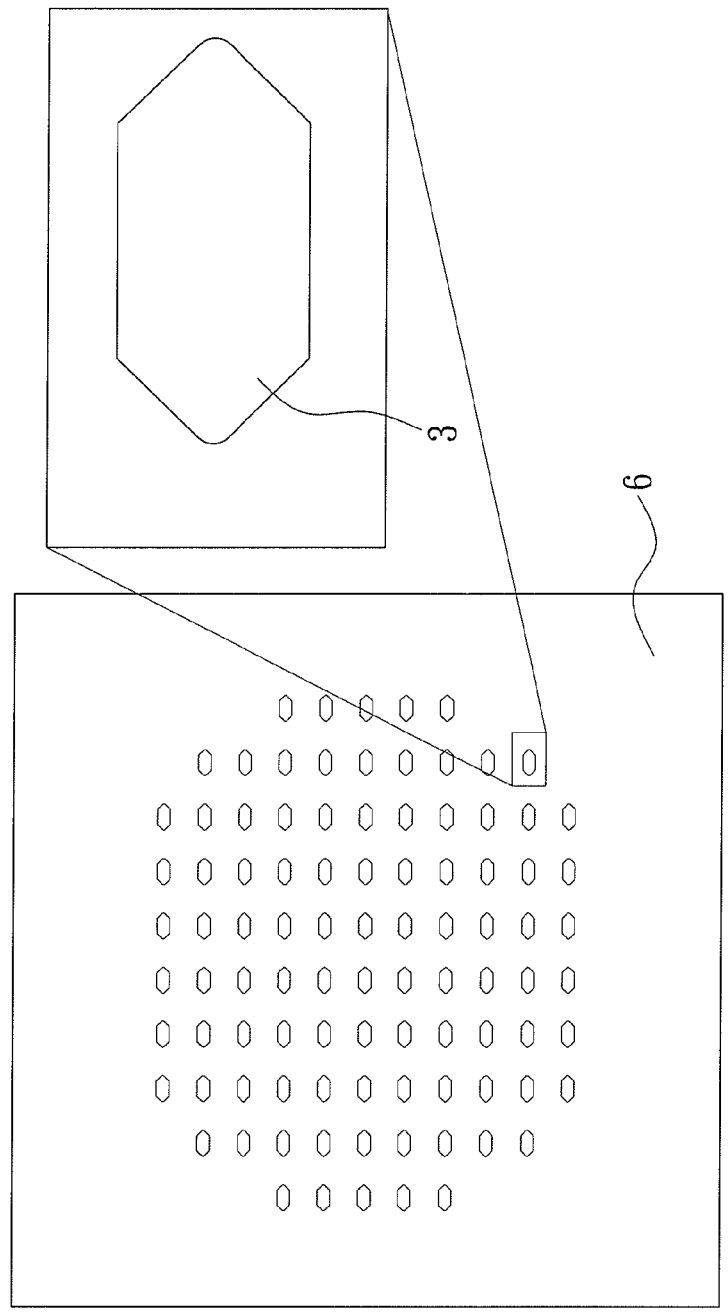
FIG. 3 shows a photomask used in the preferred embodiment of FIG. 1 for forming the patterned molecularly imprinted polymer film.

In the reaction solution 2 prepared in Example 1, the molar ratio of the anesthetic 31, the functional monomer, the crosslinking agent and the initiator with respect to each other is 1:4:30:0.41. Referring to FIG. 1 (b), the reaction solution 2 was disposed in the space defined by the lower and upper substrates 1, 10 and the spacer 5 interposed therebetween. The lower and upper substrates 1, 10 are made of cyclic olefin copolymer (COC). The spacer 5 has a thickness of 25 μm and is made of polyimide. The photomask 6 as shown in FIG. 3 was disposed on the upper substrate 10, and then, the reaction solution 2 was polymerized under a UV exposure with an irradiation energy of 40 J/cm$^2$ (wavelength: 365 nm, exposure power: 20 mW/cm$^2$, and exposure time: 2000 seconds) using a UV exposure system. Thereafter, the polymer 3 was formed on the lower substrate 1. After removing the upper substrate 10, the lower substrate 1 with the polymer 3 was dipped in a methanol solution for 24 hours to extract the anesthetic 31 from the polymer 3 and to form the MIP film 4.

EXAMPLES 2 to 10

The MIP films 4 of Examples 2 to 10 were made by the steps similar to those of Example 1, except that the thickness of the spacer 5, the exposure time and the irradiation energy setup in the UV exposure system in Examples 2 to 10 were those described in Table 1.

TABLE 1

| Example No. | Thickness of the spacer (μm) | Exposure time (sec) | Irradiation energy (J/cm$^2$) |
|---|---|---|---|
| 2 | 25 | 2400 | 48 |
| 3 | 25 | 3000 | 60 |
| 4 | 25 | 3600 | 72 |
| 5 | 50 | 1200 | 24 |
| 6 | 50 | 1500 | 30 |

TABLE 1-continued

| Example No. | Thickness of the spacer (μm) | Exposure time (sec) | Irradiation energy (J/cm$^2$) |
|---|---|---|---|
| 7 | 50 | 1800 | 36 |
| 8 | 75 | 800 | 16 |
| 9 | 75 | 1000 | 20 |
| 10 | 75 | 1200 | 24 |

EXAMPLE 11

The MIP film 4 of Example 11 was made by the steps similar to those described in Example 1, except that, in the reaction solution 2 of Example 11, the amounts of the anesthetic, the functional monomer, the crosslinking agent, and the initiator with respect to each other in the reaction solution are in a molar ratio of 1:4:30:0.17.

<Evaluation Tests>

1. Surface Topography of the Polymer 3

Figure 4:
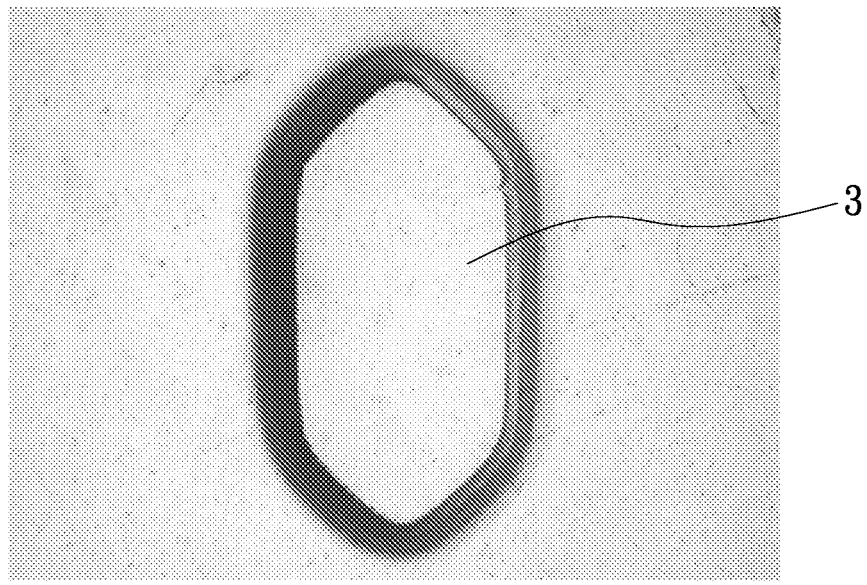
FIG. 4 is an electron microscope photograph of a polymer film of Example 1.

The surface topography of the polymer 3 of Example 1 was observed using a scanning electron microscope and the electron microscope photograph is shown in FIG. 4.

2. Surface Topography of the MIP Films 4

Figure 5:
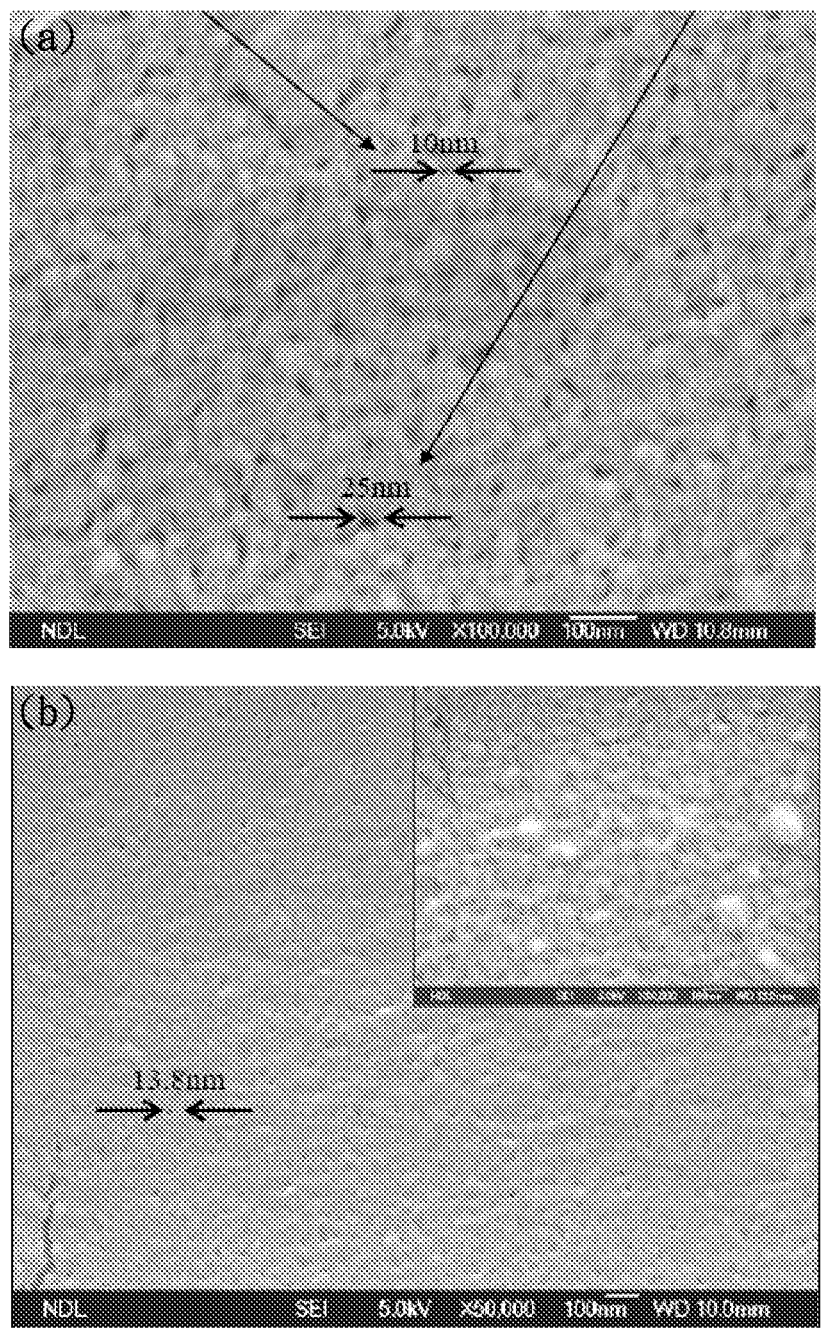
FIG. 5 are two electron microscope photographs, in which (a) shows the surface topography of the molecularly imprinted polymer film of Example 1 and (b) shows the surface topography of the molecularly imprinted polymer film of Example 3.

The surface topography of the MIP films 4 of Examples 1 and 3 were observed using the scanning electron microscope and are shown in FIG. 5, in which (a) shows the surface topography of the MIP film 4 of Example 1 and (b) shows the surface topography of the MIP film 4 of Example 3.

3. Transmittance (%) of MIP Films 4

The transmittance of the NIP film 4 of each of Examples 2 to 10 was measured using a UV spectrophotometer. The MIP films 4 were respectively removed from the lower substrates 1 of Examples 2 to 10. Each of the MIP films 4 was subsequently clamped between two quartz wafers, and the value of transmittance of each MIP film 4 is recorded in Table 2. The MIP film 4 is desired to have a relatively high transmittance.

4. Percentage Reduction (%) of MIP Films 4

The percentage reduction of the MIP film 4 of each of Examples 2 to 10 was calculated based on the following equation (I) and is recorded in Table 2:

Percentage reduction(%)=(an area of the MIP film/an area of each pattern unit of the photomask)×100%    (I).

The area of the MIP film 4 was calculated using an Image J program based on a photograph of the MIP film 4 taken by a digital camera with the MIP film 4 removed from the lower substrate 1 and clamped between two substrates made of polyolefin copolymer.

The MIP film 4 is desired to have a relatively high percentage reduction.

5. Percentage Expansion (%) of MIP Films 4

The percentage expansion of the MIP film 4 of each of Examples 2 to 10 was calculated based on the following equation (II) and is recorded in Table 2:

Percentage expansion(%)=(the area of the wetted MIP film/the area of the MIP film)×100%    (II).

The wetted MIP was obtained by impregnating the MIP film 4 with methanol. The areas of the MIP film 4 and the wetted MIP film were calculated by the method for measuring the area of the MIP film 4 described in the paragraph of the percentage reduction.

The MIP film 4 is preferred to have a relatively low percentage expansion.

6. Adsorption Amount (μg/mm$^2$) of MIP Films 4

Three anesthetic solutions, i.e., 0.7918 μg/mL, 7.918 μg/mL and 19.795 μg/mL of propofol in methanol, were prepared by dissolving appropriate amounts of propofol in methanol.

The MIP films 4 obtained from Examples 1 and 3 were respectively dipped in 2 grams of the above three anesthetic solutions for 15 minutes. The adsorption amount of the MIP film 4 of each of Examples 1 and 3 in each of the three anesthetic solutions was calculated based on the following equation (III) and is recorded in Table 3:

Adsorption amount(μg/mm$^2$)=[(the concentration of an anesthetic solution before dipping of the MIP film 4–the concentration of the anesthetic solution after dipping of the MIP film 4)×2]/the area of the MIP film 4    (III).

7. Specific Binding Rate(%) of MIP Films 4

The specific binding rate of the MIP film 4 of each of Examples 1 and 3 was calculated based on the following equation (IV) and is recorded in Table 3.

Specific binding rate(%)=(the adsorption amount of the MIP film 4/an adsorption amount of a NIP film)×100%    (IV)

The NIP film means non-imprinted polymer film, and was formed by the same method for making the MIP film 4 except that the reaction solution for making the NIP film did not include the anesthetic. The adsorption amount of the MIP film 4 or the NIP film was measured according to the paragraph of the adsorption amount.

TABLE 2

| Example | Transmittance (%) | Percentage reduction (%) | Percentage expansion (%) |
|---|---|---|---|
| 2 | 88.87 | 87.57 | 106.19 |
| 3 | 90.55 | 84.93 | 108.30 |
| 4 | 89.80 | 86.59 | 107.41 |
| 5 | 88.45 | 80.05 | 113.61 |
| 6 | 90.19 | 85.57 | 107.06 |
| 7 | 90.39 | 88.18 | 107.01 |
| 8 | 87.98 | 88.24 | 108.52 |
| 9 | 88.91 | 90.89 | 104.62 |
| 10 | 88.70 | 88.24 | 107.35 |

TABLE 3

| Conc. of anesthetic solutions (μg/mL) | Adsorption amount (μg/mm$^2$) | | | | Specific binding rate (%) | |
|---|---|---|---|---|---|---|
| | Ex. 1 | | Ex. 3 | | | |
| | NIP | MIP | NIP | MIP | Ex. 1 | Ex. 3 |
| 0.7918 | 0.00051 | 0.00233 | 0.00051 | 0.00098 | 455.82 | 191.53 |
| 7.918 | 0.00947 | 0.02330 | 0.00368 | 0.00607 | 246.09 | 164.84 |
| 19.795 | 0.03989 | 0.05521 | 0.00793 | 0.02137 | 138.40 | 269.56 |

Referring to the electron microscope photograph of FIG. 4, it is observed that the polymer 3 obtained from Example 1 was completely polymerized. However, the polymer 3 obtained from the Example 11 is partially but acceptably polymerized. Apparently, when the molar ratio of the initiator with respect to the anesthetic 31, the functional monomer, and the crosslinking agent is lower than 0.17, the polymerization degree of the polymer 3 is unacceptable. Accordingly, it is evident that by controlling the molar ratio of the initiator in the reaction solution 2, the polymerization degree of the reaction solution 2 can be adjusted, and that the lower limit of the molar ratio of the anesthetic 31, the functional monomer, the crosslinking agent and the initiator with respect to each other in the reaction solution is preferred to be at least 1:4:30:0.17.

In FIG. 5, (a) shows that the MIP film 4 of Example 1 has a plurality of pores with a pore size ranging from 10 nm to 25 nm, and (b) shows that the MIP film 4 of Example 3 has a plurality of pores with a pore size of about 13.8 nm. Therefore, by the method of the present invention, the MIP film 4 can be formed with a plurality of pores having a relatively small size (10 nm~25 nm).

Besides, from the data of evaluation tests shown in Table 2, it is found that the transmittance, the percentage reduction and the percentage expansion for each of the MIP films 4 made according to the method of this invention conform with the commercial requirements.

As shown in Table 3, when the MIP film 4 was dipped in the anesthetic solutions of different concentrations, the MIP film 4 can exhibit differences in the adsorption amount (0.00098~0.05521 μg/mm$^2$) and the specific binding rate (164.84%~455.82%). Therefore, the MIP film 4 of the present invention can be used in the MIP biosensor for detecting the anesthetic 31, especially the anesthetics of small molecules, such as propofol. Furthermore, the MIP biosensor having the MIP film 4 can exhibit relatively good sensitivity.

In summary, by controlling the molar ratio of the initiator in the reaction solution 2 and by polymerizing the reaction solution 2 under an irradiation energy of a specific range, the MIP film 4 can be formed with the pores having appropriate sizes.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

What is claimed is:

1. A method for forming a molecularly imprinted polymer biosensor, comprising:
    (a) preparing a reaction solution including an imprinting molecule, a functional monomer, an initiator, and a crosslinking agent, wherein a molar ratio of the imprinting molecule, the functional monomer, the initiator and the crosslinking agent with respect to each other in the reaction solution ranges from about 1:4:30:0.17 to 1:4:30:0.85;
    (b) disposing the reaction solution in a space between upper and lower substrates each of which is made of a light-transmissible material;
    (c) disposing on the upper substrate a photomask having a patterned hole;
    (d) irradiating the reaction solution through the patterned hole of the photomask and the upper substrate so that the reaction solution undergoes polymerization to form a polymer between the upper and lower substrates, wherein step (d) is conducted with an irradiation energy ranging from 16 J/cm$^2$ to 72 J/cm$^2$;
    (e) removing the upper substrate after the polymer is formed on the lower substrate; and
    (f) extracting the imprinting molecule from the polymer so that a patterned molecularly imprinted polymer film is formed on the lower substrate.

2. The method of claim 1, further comprising bonding a microchannel substrate to the lower substrate having the patterned molecularly imprinted polymer film.

3. The method of claim 1, wherein the imprinting molecule is anesthetic.

4. The method of claim 3, wherein the anesthetic is propofol.

5. The method of claim 1, wherein the light-transmissible material is a cyclic olefin copolymer.

6. The method of claim 1, wherein the molecularly imprinted polymer film has a thickness ranging from 25 μm to 75 μm.

7. The method of claim 1, wherein the molecularly imprinted polymer film has a plurality of pores with a pore size ranging from 10 nm to 30 nm.

8. The method of claim 1, wherein the molecularly imprinted polymer film has a plurality of pores, wherein said pores are formed without using a solvent or a porogen.

9. The method of claim 1, wherein the molecularly imprinted polymer film has a plurality of pores, wherein said pores are formed without using grinding.

10. The method of claim 7, wherein the pores of the molecularly imprinted polymer film are formed without using a solvent or a porogen.

11. The method of claim 7, wherein the pores of the molecularly imprinted polymer film are formed without using grinding.

12. The method of claim 1, wherein the molar ratio of the imprinting molecule, the functional monomer, the initiator and the crosslinking agent with respect to each other in the reaction solution ranges from about 1:4:30:0.3 to 1:4:30:0.5.

13. The method of claim 1, wherein the molar ratio of the imprinting molecule, the functional monomer, the initiator and the crosslinking agent with respect to each other in the reaction solution is 1:4:30:0.41.

* * * * *